United States Patent
Wiederin et al.

(10) Patent No.: US 9,953,822 B1
(45) Date of Patent: Apr. 24, 2018

(54) CHROMATOGRAPHIC OFFLINE SAMPLE PREPARATION AND STORAGE FOR SAMPLE ANALYSIS

(71) Applicant: Elemental Scientific, Inc., Omaha, NE (US)

(72) Inventors: Daniel R. Wiederin, Omaha, NE (US); Paul Field, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 0 days.

(21) Appl. No.: 14/740,472

(22) Filed: Jun. 16, 2015

Related U.S. Application Data

(63) Continuation of application No. 14/583,896, filed on Dec. 29, 2014, now abandoned.

(60) Provisional application No. 61/921,923, filed on Dec. 30, 2013.

(51) Int. Cl.
| | |
|---|---|
| *G01N 30/46* | (2006.01) |
| *H01J 49/10* | (2006.01) |
| *H01J 49/00* | (2006.01) |
| *G01N 30/72* | (2006.01) |
| *G01N 30/74* | (2006.01) |
| *G01J 3/443* | (2006.01) |

(52) U.S. Cl.
CPC ............. *H01J 49/105* (2013.01); *G01J 3/443* (2013.01); *G01N 30/7253* (2013.01); *G01N 30/74* (2013.01); *H01J 49/0031* (2013.01)

(58) Field of Classification Search
CPC ...... G01N 30/461; G01N 30/46; G01N 30/26; B01D 15/1871; B01D 15/1864; B01D 15/18; B01D 15/08; Y10T 436/20; Y10T 436/207497; H01J 49/105; H01J 49/10; H01J 49/02

USPC .............. 436/136, 127; 422/81, 70, 69, 68.1
See application file for complete search history.

(56) References Cited

U.S. PATENT DOCUMENTS

| | | | |
|---|---|---|---|
| 6,344,172 B1 * | 2/2002 | Afeyan | G01N 30/461 210/198.2 |
| 2007/0104471 A1 * | 5/2007 | Hannigan | H01J 49/0422 392/478 |
| 2007/0272605 A1 * | 11/2007 | Lundblad | G01N 30/82 210/198.2 |

OTHER PUBLICATIONS

Stephen Romaniello, Gwyneth W. Gordon, Dan Wiederin, M. Paul Field and Ariel D. Anbar; Automated sample purification: Radiogenic and non-traditional metal isotopes in the 21st century; Goldschmidt 2012 Conference Abstracts; Mineralogical Magazine; www.minersoc.org.

* cited by examiner

*Primary Examiner* — Christine T Mui
(74) *Attorney, Agent, or Firm* — Advent, LLP

(57) ABSTRACT

A system includes a sample selector device, a chromatographic column selectively connectable to the sample selector device, and a spectrometry analysis device selectively connectable to the sample selector device. The sample selector device is configured to supply multiple individual samples to the chromatographic column to separate components of the individual samples. The sample selector device is also configured to store the separated components of the individual samples. The sample selector device is further configured to supply the separated components of the individual samples to the spectrometry analysis device. In embodiments of the disclosure, the components of the individual samples can be chromatographically separated while the spectrometry analysis device is offline.

20 Claims, 2 Drawing Sheets

CHROMATOGRAPHIC OFFLINE SAMPLE PREPARATION AND STORAGE FOR SAMPLE ANALYSIS

CROSS-REFERENCE TO RELATED APPLICATIONS

The present application is a continuation under 35 U.S.C. § 120 of U.S. patent application Ser. No. 14/583,896, filed Dec. 29, 2014, and titled "OFFLINE AUTOMATED SAMPLE PREPARATION," which claims priority under 35 U.S.C. § 119(e) of U.S. Provisional Application Ser. No. 61/921,923, filed Dec. 30, 2013, and titled "OFFLINE AUTOMATED SAMPLE PREPARATION." U.S. patent application Ser. No. 14/583,896 and U.S. Provisional Application Ser. No. 61/921,923 are herein incorporated by reference in their entireties.

SUMMARY

A system includes a sample selector device, a chromatographic column selectively connectable to the sample selector device, and a spectrometry analysis device selectively connectable to the sample selector device. The sample selector device is configured to supply multiple individual samples to the chromatographic column to separate components of the individual samples. The sample selector device is also configured to store the separated components of the individual samples. The sample selector device is further configured to supply the separated components of the individual samples to the spectrometry analysis device. In embodiments of the disclosure, the components of the individual samples can be chromatographically separated while the spectrometry analysis device is offline.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures.

DETAILED DESCRIPTION

Figure 1:
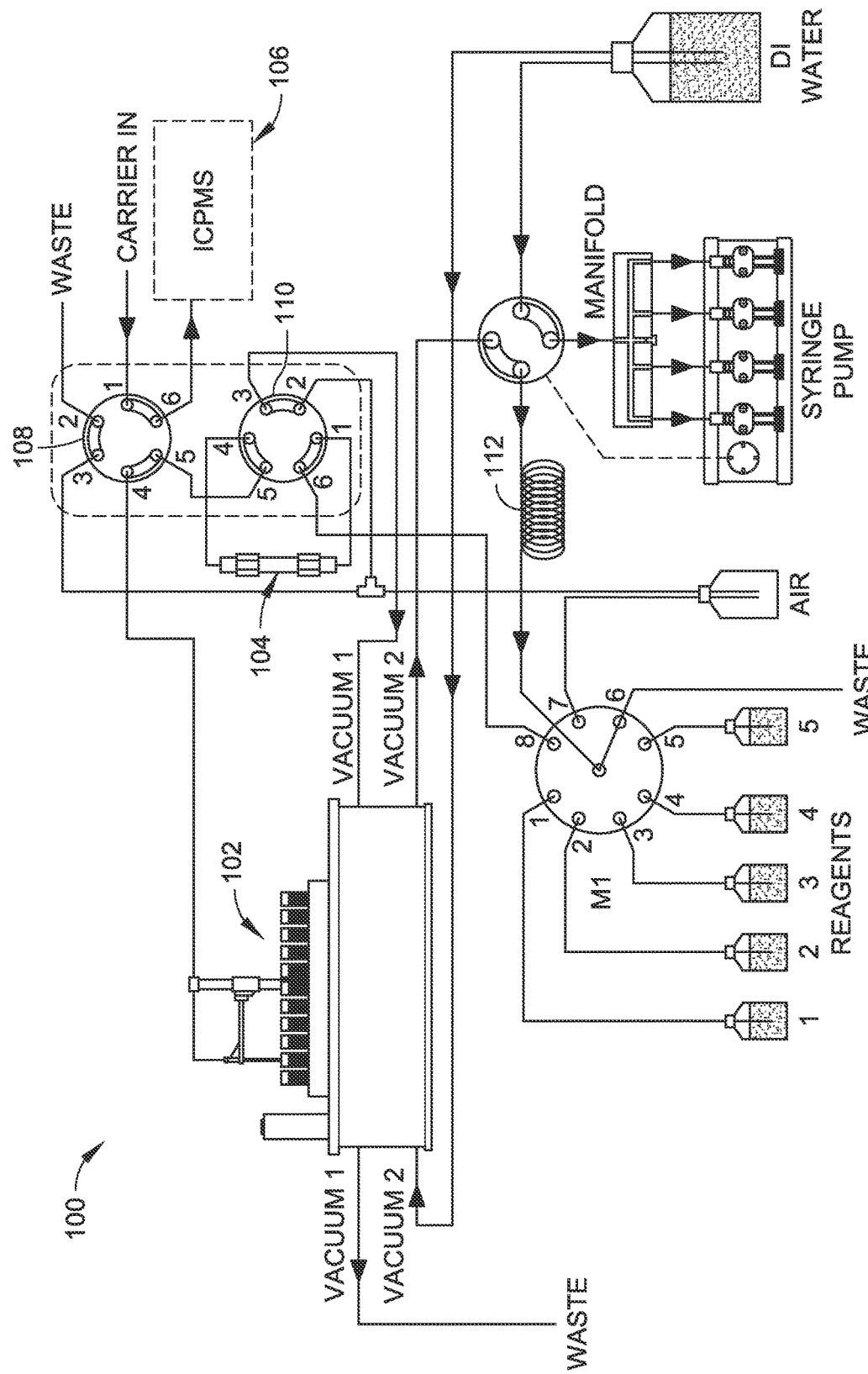
FIG. 1 is a diagrammatic illustration of a system for separating components from multiple samples offline and storing the components in preparation for sample analysis in accordance with example embodiments of the present disclosure.

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

Liquid chromatography is a chromatographic technique used to separate a mixture of compounds for identifying, quantifying, and/or purifying individual components of the mixture. Chromatography can be described as a mass transfer process involving adsorption. A liquid and a sample mixture are passed through a column filled with a sorbent, leading to separation of the sample components. The active component of the column, the sorbent, is typically a granular material made of solid particles (e.g. silica, polymers, etc.). The components of the sample mixture are separated from each other due to their different degrees of interaction with the sorbent particles. The liquid is typically a mixture of solvents (e.g. water, acetonitrile, and/or methanol) and is referred to as "mobile phase." Generally, liquid chromatography relies on the force of gravity to pass the mobile phase through the column. High-performance liquid chromatography (HPLC) uses a pump to pass pressurized liquid and sample mixture through a column.

Referring generally to the accompanying figures, a system is described for facilitating a procedure. The system includes a sample selector device (e.g., an autosampler), one or more valves (e.g., three (3) valves, including two (2) two-position valves and one (1) multi-position valve), a pump device (e.g., one or more syringe pumps), tubing segments (e.g., for coupling the sample selector device, the valve(s), and the pump device), and a non-transitory computer-readable storage medium. The non-transitory computer-readable storage medium has computer executable instructions configured to instruct a user to configure (e.g., assemble) the sample selector device, the valve(s), the pump device, and the tubing segments to facilitate a laboratory procedure. For example, the system can be used to facilitate a laboratory procedure that uses ICP spectrometry (e.g., ICP-MS, ICP-AES, and so forth), liquid chromatography (e.g., HPLC), and so on. In some embodiments, the sample selector device, the valve(s), the pump device, and the tubing segments are connected to a chromatography column. In other embodiments, the sample selector device, the valves, the pump device, and the tubing segments are connected to a plasma torch assembly. In further embodiments, the sample selector device, the valves, the pump device, and the tubing segments are connected to a chromatography column and a plasma torch assembly.

The system can be configured for particular timing, volumes, flow rates, and so forth specific to a particular (e.g., precise) laboratory procedure (e.g., detecting uranium isotopes, detecting strontium isotopes, detecting boron isotopes, detecting bio-available metals, applications requiring sample purification for metals, detecting metals in ocean seawater, detecting Rare Earth Elements (REEs) in ocean seawater, and so forth). For example, particular tubing lengths, particular volumes to be controlled by the pump device, particular reagents, and so on are specified by the non-transitory computer-readable storage medium for a particular chemistry. For example, the non-transitory computer-readable storage medium includes a database of chemistries, plumbing, and valve configurations tailored to one or more laboratory procedures. In this manner, the system can be set up in real time (e.g., in ICP-MS), and further analysis can be performed offline. The computer executable instructions of the non-transitory computer-readable storage medium can also be configured to analyze information (e.g., measurements) obtained from the laboratory procedure (e.g., to detect an element concentration, an isotope ratio, and so forth).

Referring now to FIG. 1, a system 100 is described. The system 100 can include a sample selector device 102 (e.g., an autosampler), one or more columns 104 (e.g., chromatographic columns), and a spectrometry analysis device 106 (e.g., an ICPMS). In embodiments of the disclosure, the column 104 and the spectrometry analysis device 106 can be selectively connectable to the sample selector device 102. For example, a first valve 108 and a second valve 110 can be used to selectively connect the sample selector device 102 to the column 104 and the spectrometry analysis device 106. In this manner, the system 100 can be used to chromatographically separate components of individual samples while the spectrometry analysis device 106 is offline.

The sample selector device 102 is configured to supply multiple individual samples to the column 104 to separate components of the individual samples. In some embodiments, liquid and a sample mixture can be passed through the column 104, which can be filled with a sorbent, leading to separation of sample components. For example, the sorbent can be a granular material made of solid particles, and components of the sample mixture can be separated due to their different degrees of interaction with the sorbent particles. The sample selector device 102 is also configured to store the separated components of the individual samples. For instance, sample is supplied from the sample selector device 102 to fill a sample loop 112. The sample loop 112 is then dispensed onto the column 104. One or more components of the sample are then eluted from the column 104 and stored at the sample selector device 102 (e.g., in a destination vial). Then, the sample selector device 102 can supply the separated components of the individual samples to the spectrometry analysis device 106 (e.g., from multiple destination vials).

Figure 2:
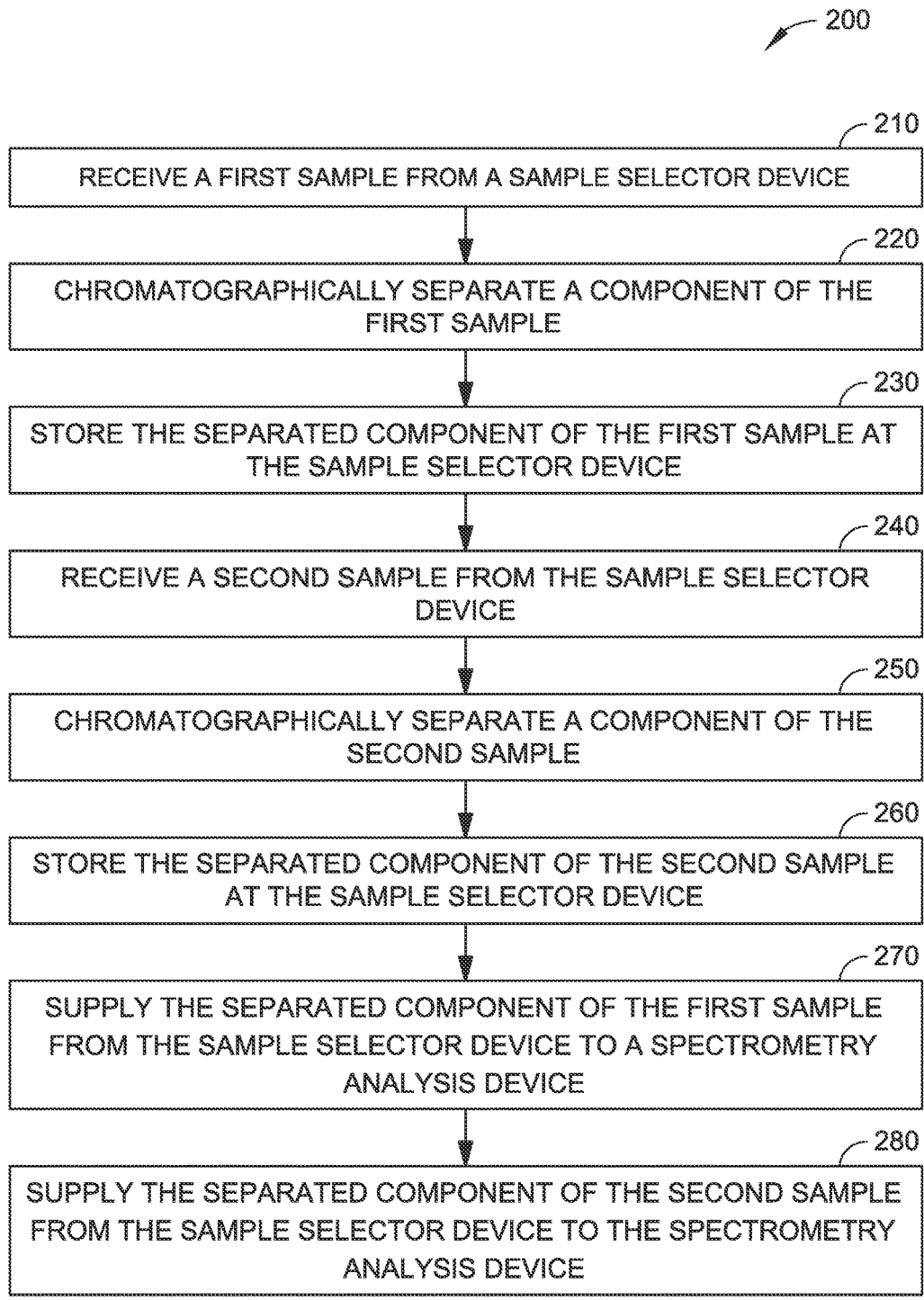
FIG. 2 is a flow diagram illustrating a method of separating components from multiple samples offline and storing the components in preparation for sample analysis in accordance with example embodiments of the present disclosure.

FIG. 2 depicts a procedure 200 in an example implementation in which components are separated from multiple samples offline and stored in preparation for sample analysis. As shown in FIG. 2, a first sample is received from a sample selector device (Block 210). For example, with reference to FIG. 1, sample is supplied from the sample selector device 102 to fill the sample loop 112. The sample loop 112 is then dispensed onto the column 104. Next, one or more components are chromatographically separated from the first sample (Block 220). For instance, with continuing reference to FIG. 1, one or more components of the sample are eluted from the column 104. Then, the separated component or components of the first sample are stored at the sample selector device (Block 230). For example, with continuing reference to FIG. 1, one or more components of the sample are stored at the sample selector device 102 (e.g., in a destination vial).

Next, a second sample is received from the sample selector device (Block 240). For instance, with reference to FIG. 1, another sample is supplied from the sample selector device 102 to fill the sample loop 112. The sample loop 112 is then dispensed onto the column 104. Then, one or more components are chromatographically separated from the second sample (Block 250). For example, with continuing reference to FIG. 1, one or more components of the second sample are eluted from the column 104. Next, the separated component or components of the second sample are stored at the sample selector device (Block 260). For instance, with continuing reference to FIG. 1, one or more components of the second sample are stored at the sample selector device 102 (e.g., in a different destination vial).

Then, one or more components separated from the first sample are supplied from the sample selector device to a spectrometry analysis device (270). For example, with continuing reference to FIG. 1, the sample selector device 102 supplies the separated components of the first sample to the spectrometry analysis device 106 (e.g., from the first destination vial). Next, one or more components separated from the second sample are supplied from the sample selector device to the spectrometry analysis device (280). For instance, with continuing reference to FIG. 1, the sample selector device 102 supplies the separated components of the second sample to the spectrometry analysis device 106 (e.g., from the second destination vial). In this manner, components of the first sample and the second sample can be separated while the spectrometry analysis device 106 is offline. It should be noted that while chromatographic separation of components of two different samples has been described with reference to FIG. 2, this example is provided by way of example only. In other embodiments, more than two samples (e.g., fifty samples, one hundred samples, etc.) can be chromatographically separated (e.g., while the spectrometry analysis device 106 is offline) and subsequently supplied to the spectrometry analysis device 106.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:
1. A system comprising:
a sample selector device;
a chromatographic column selectively connectable to the sample selector device, the sample selector device configured to supply a first sample to the chromatographic column to separate at least one component of the first sample and supply a second sample to the chromatographic column to separate at least one component of the second sample, the sample selector device further configured to store the at least one separated component of the first sample and the at least one separated component of the second sample; and
a spectrometry analysis device selectively connectable to the sample selector device, the sample selector device configured to supply the at least one separated component of the first sample to the spectrometry analysis device and supply the at least one separated component of the second sample to the spectrometry analysis device, the at least one component of the first sample and the at least one component of the second sample separated by being eluted from the chromatographic column while the spectrometry analysis device is offline.

2. The system as recited in claim 1, wherein the sample selector device comprises an autosampler.

3. The system as recited in claim 1, wherein the spectrometry analysis device comprises an inductively coupled plasma spectrometry device.

4. The system as recited in claim 3, wherein the inductively coupled plasma spectrometry device comprises at least one of an inductively coupled plasma mass spectrometer or an inductively coupled plasma atomic emission spectrometer.

5. The system as recited in claim 1, further comprising a pump for pressurizing the samples supplied to the chromatographic column.

6. The system as recited in claim 1, further comprising a multi-position valve for selectively providing at least one of a plurality of reagents to the chromatographic column.

7. The system as recited in claim 1, further comprising a syringe pump coupled with the sample selector device for supplying the first sample to the chromatographic column.

8. A method comprising:
receiving a first sample from a sample selector device;
chromatographically separating at least one component of the first sample;
storing the at least one separated component of the first sample at the sample selector device;
receiving a second sample from the sample selector device;
chromatographically separating at least one component of the second sample;
storing the at least one separated component of the second sample at the sample selector device;
supplying the at least one separated component of the first sample from the sample selector device to a spectrometry analysis device;
supplying the at least one separated component of the second sample from the sample selector device to the spectrometry analysis device, the at least one component of the first sample and the at least one component of the second sample separated by being eluted from the chromatographic column while the spectrometry analysis device is offline.

9. The method as recited in claim 8, wherein the sample selector device comprises an autosampler.

10. The method as recited in claim 8, wherein the spectrometry analysis device comprises an inductively coupled plasma spectrometry device.

11. The method as recited in claim 10, wherein the inductively coupled plasma spectrometry device comprises at least one of an inductively coupled plasma mass spectrometer or an inductively coupled plasma atomic emission spectrometer.

12. The method as recited in claim 8, wherein at least one of the first sample or the second sample is supplied to the chromatographic column under pressure.

13. The method as recited in claim 8, wherein at least one of a plurality of reagents is selectively provided to the chromatographic column using a multi-position valve.

14. The method as recited in claim 8, wherein the first sample is supplied to the chromatographic column by a syringe pump coupled with the sample selector device.

15. A system comprising:
a sample selector device;
a chromatographic column selectively connectable to the sample selector device, the sample selector device configured to supply a first sample to the chromatographic column to separate at least one component of the first sample and supply a second sample to the chromatographic column to separate at least one component of the second sample, the sample selector device further configured to store the at least one separated component of the first sample and the at least one separated component of the second sample;
a spectrometry analysis device selectively connectable to the sample selector device, the sample selector device configured to supply the at least one separated component of the first sample to the spectrometry analysis device and supply the at least one separated component of the second sample to the spectrometry analysis device, the at least one component of the first sample and the at least one component of the second sample separated by being eluted from the chromatographic column while the spectrometry analysis device is offline; and
a syringe pump coupled with the sample selector device for supplying the first sample and the second sample to the chromatographic column.

16. The system as recited in claim 15, wherein the sample selector device comprises an autosampler.

17. The system as recited in claim 15, wherein the spectrometry analysis device comprises an inductively coupled plasma spectrometry device.

18. The system as recited in claim 17, wherein the inductively coupled plasma spectrometry device comprises at least one of an inductively coupled plasma mass spectrometer or an inductively coupled plasma atomic emission spectrometer.

19. The system as recited in claim 15, further comprising a pump for pressurizing the samples supplied to the chromatographic column.

20. The system as recited in claim 15, further comprising a multi-position valve for selectively providing at least one of a plurality of reagents to the chromatographic column.

* * * * *